United States Patent
Axness

(10) Patent No.: US 10,238,881 B2
(45) Date of Patent: Mar. 26, 2019

(54) PREVENTION OF INADVERTENT BATTERY DEPLETION IN AN AUTOMATIC EXTERNAL DEFIBRILLATOR

(71) Applicant: KONINKLIJKE PHILIPS N.V., Eindhoven (NL)

(72) Inventor: David Roy Axness, Fall City, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 479 days.

(21) Appl. No.: 14/780,795

(22) PCT Filed: Mar. 29, 2014

(86) PCT No.: PCT/IB2014/060295
§ 371 (c)(1),
(2) Date: Sep. 28, 2015

(87) PCT Pub. No.: WO2014/155367
PCT Pub. Date: Oct. 2, 2014

(65) Prior Publication Data
US 2016/0045753 A1    Feb. 18, 2016

Related U.S. Application Data

(60) Provisional application No. 61/806,422, filed on Mar. 29, 2013.

(51) Int. Cl.
*A61N 1/39* (2006.01)
(52) U.S. Cl.
CPC .................................. *A61N 1/3931* (2013.01)
(58) Field of Classification Search
CPC .............. A61N 1/37247; A61N 1/3925; A61N 1/3993; A61N 1/37235; A61N 1/39; A61N 1/046; A61N 1/3968; A61N 1/3937; A61N 1/36014; A61N 1/36132; A61N 1/36139; A61N 1/37211; A61N 1/36125; A61N 1/37217; A61N 1/3975; A61N 1/36128; A61N 1/36142; A61N 1/362; A61N 1/378;
(Continued)

(56) References Cited

U.S. PATENT DOCUMENTS

| 5,249,298 A | 9/1993 | Bolan et al. |
| 6,083,246 A | 7/2000 | Stendahl et al. |

(Continued)

FOREIGN PATENT DOCUMENTS

| EP | 0701196 A2 | 3/1996 |
| JP | 2011067651 A | 4/2011 |

(Continued)

OTHER PUBLICATIONS

"AED 10 (TM) Automated External Defibrillator"; User Manual, Software Version 2.07.XX, Welch Allyn, Jul. 2009, 92 Page Document.

(Continued)

*Primary Examiner* — Deborah Malamud

(57) ABSTRACT

A defibrillator (100) and method (300) are described having an improved automatic activation feature. The improvement comprises sensing a pattern of events which indicates that repeated activations are inadvertent, and thus are unnecessarily depleting the battery. The defibrillator then disables the automatic activation circuit (210) feature. Then, the sensing of a manual defibrillator operation may trigger a re-enablement of the automatic activation feature.

18 Claims, 3 Drawing Sheets

(58) Field of Classification Search
CPC .. A61N 1/0484; A61N 1/0553; A61N 1/3625;
A61N 1/375; A61N 2001/083; A61N
1/04; A61N 1/0472; A61N 1/0476; A61N
1/08; A61N 1/18; A61B 5/4836; A61B
5/486; A61B 5/0408; A61B 5/044; A61B
5/046; A61B 5/6831; A61B 2560/0209;
A61B 2560/0214; A61B 2560/0276;
A61B 5/6802; G06F 19/3412; A61H
31/005; A61H 31/004; A61H 31/006;
G06Q 50/22
See application file for complete search history.

(56) References Cited

U.S. PATENT DOCUMENTS

| | | |
|---|---|---|
| 6,169,387 B1 | 1/2001 | Kaib |
| 2003/0208237 A1 | 11/2003 | Locke et al. |
| 2006/0129191 A1 | 6/2006 | Sullivan et al. |

FOREIGN PATENT DOCUMENTS

| | | |
|---|---|---|
| RU | 2004134420 A | 5/2006 |
| WO | 03020362 A2 | 3/2003 |
| WO | 03053519 A2 | 7/2003 |
| WO | 2012063160 A1 | 5/2012 |

OTHER PUBLICATIONS

Carroll et al: "An Analysis of Power Consumption in a Smartphone"; Published in : Proceedings of the 2010 USENIX, USENIXATC'10. 20 Pages.

PREVENTION OF INADVERTENT BATTERY DEPLETION IN AN AUTOMATIC EXTERNAL DEFIBRILLATOR

CROSS-REFERENCE TO PRIOR APPLICATIONS

This application is the U.S. National Phase application under 35 U.S.C. § 371 of International Application No. PCT/IB2014/060295, filed on Mar. 29, 2014, which claims the benefit of U.S. Provisional Patent Application No. 61/806,422, filed on Mar. 29, 2013. These applications are hereby incorporated by reference herein.

FIELD OF THE INVENTION

This invention relates to battery powered medical devices used in cardiac resuscitation rescues and, in particular, to defibrillators.

BACKGROUND OF THE INVENTION

Cardiac arrest is a life-threatening medical condition in which the patient's heart fails to provide blood flow to support life. A defibrillator can be used to deliver defibrillating shocks to a patient suffering from cardiac arrest. The defibrillator resolves this condition by delivering a high-voltage impulse to the heart in order to restore normal rhythm and contractile function in patients who are experiencing arrhythmia such as VF (ventricular fibrillation) or VT (ventricular tachycardia) that is not accompanied by spontaneous circulation. One type of defibrillator, the automated external defibrillator (AED), differs from manual defibrillators in that the AED can automatically analyze the electrocardiogram (ECG) rhythm to determine if defibrillation is necessary. The defibrillator analyzes the ECG signal for signs of arrhythmia. If VF is detected, the defibrillator signals the rescuer that a shock is advised. After the detection of VF or other shockable rhythm, the rescuer presses a shock button on the defibrillator to deliver a defibrillation pulse to resuscitate the patient.

Defibrillation must be delivered very soon after the onset of cardiac arrest in order to be effective. It is estimated that the chance of survival falls by 10% for every minute of delay to defibrillation beyond four minutes after cardiac arrest. Hence, AEDs are designed to be used by first responders, such as firefighters, police, or lay bystanders, who are the most likely to arrive at the patient's side first. Once an AED is brought to the patient, the rescuer must deploy and use it quickly.

Some prior art defibrillators are designed to power on automatically when the defibrillator carry case is opened in order to minimize the time until the AED is ready to delivery therapy. For example, U.S. Pat. No. 6,083,246, entitled "Lid open detection circuit for automated external defibrillators" by Stendahl et al. describes an AED which automatically activates when a lid is opened to deploy the electrodes inside. Another co-assigned application, PCT/IB2011/054822 entitled "CARRYING CASE WITH IMPROVED ACCESS FOR DEFIBRILLATOR AND ACCESSORIES" by Roach et al. and herein incorporated by reference, describes a defibrillator system in which a carrying case has a lid open sensor for automatically activating the defibrillator inside when the case is opened.

AEDs often include electrodes and other accessories which aid in the administration of cardiopulmonary resuscitation (CPR) during the rescue. FIG. 1 illustrates one defibrillator carrying case, in which a set of patient electrodes 140 and a fast response kit 130 are stored within the case with the AED itself.

Such prior art defibrillators are portable and battery powered. Each time that the defibrillator is automatically activated by opening the lid, the battery suffers some depletion. It is important then that the automatic activation is intended for some purpose. Otherwise, the defibrillator battery is unnecessarily depleted, which costs money and potentially delays therapy while the depleted battery is changed out.

Inadvertent activation of the defibrillator can occur for a variety of reasons. The carry case latch may fail in a way that is not readily observable by the owner. The automatic power on sensor may malfunction and issue spurious activation indications to the device. More commonly, the carry case becomes overstuffed with accessories, which causes the case to become distorted such that the case opening sensor activates. Any of these problems would cause the automatic power on feature to unnecessarily activate the defibrillator and deplete the battery. What is needed then is a solution to this problem.

SUMMARY OF THE INVENTION

In accordance with the objectives of the present invention, an improved automatic power on feature for a defibrillator is described which detects likely circumstances of inadvertent activation. The invention generally encompasses the detecting that there is a pattern of the defibrillator powering on automatically and not being used for therapy or diagnostic evaluation, e.g. a typical intended use. When the defibrillator detects such a pattern of events, the automatic power on feature is disabled. Then, when the AED is used in a manner that indicates the AED has been handled by a human such as replacing the battery or powering on the AED manually via the on/off switch, the automatic power on feature is re-enabled.

The invention is disposed such that a routine maintenance event such as opening the case on a regular basis (such as once per shift) to verify contents/expiration dates of items in the carry case will not cause the automatic power on feature to be disabled.

In accordance with the objectives of the invention, a portable defibrillator apparatus is described comprising an electrode connector, an operator actuated button, an automatic power on circuit which is operable to actuate the defibrillator independent of the operator actuated button, and a controller in electrical communication with the electrode connector, the operator actuated button and the automatic power on circuit. The controller is operable to detect a pattern of events and is further operable to disable the automatic power on circuit in response to the detected pattern of events.

In accordance with yet another aspect of the invention, a method for managing a power condition of a defibrillator is described, comprising a first step of providing a defibrillator in a low power standby condition, the defibrillator including a controller in electrical communication with an electrode connector, an operator actuated button, and an automatic power on circuit operable to actuate the defibrillator independent of the operator actuated button. The method also includes the steps of automatically activating the defibrillator with the automatic power on circuit, detecting a pattern of events based on the automatically activating step, disabling the automatic power on circuit based on the detecting step, and returning the defibrillator to the low power standby condition with the automatic power on circuit disabled. The method also includes optionally re-enabling the automatic power on circuit by means of a subsequent user action.

DETAILED DESCRIPTION OF THE EMBODIMENTS

Figure 1:
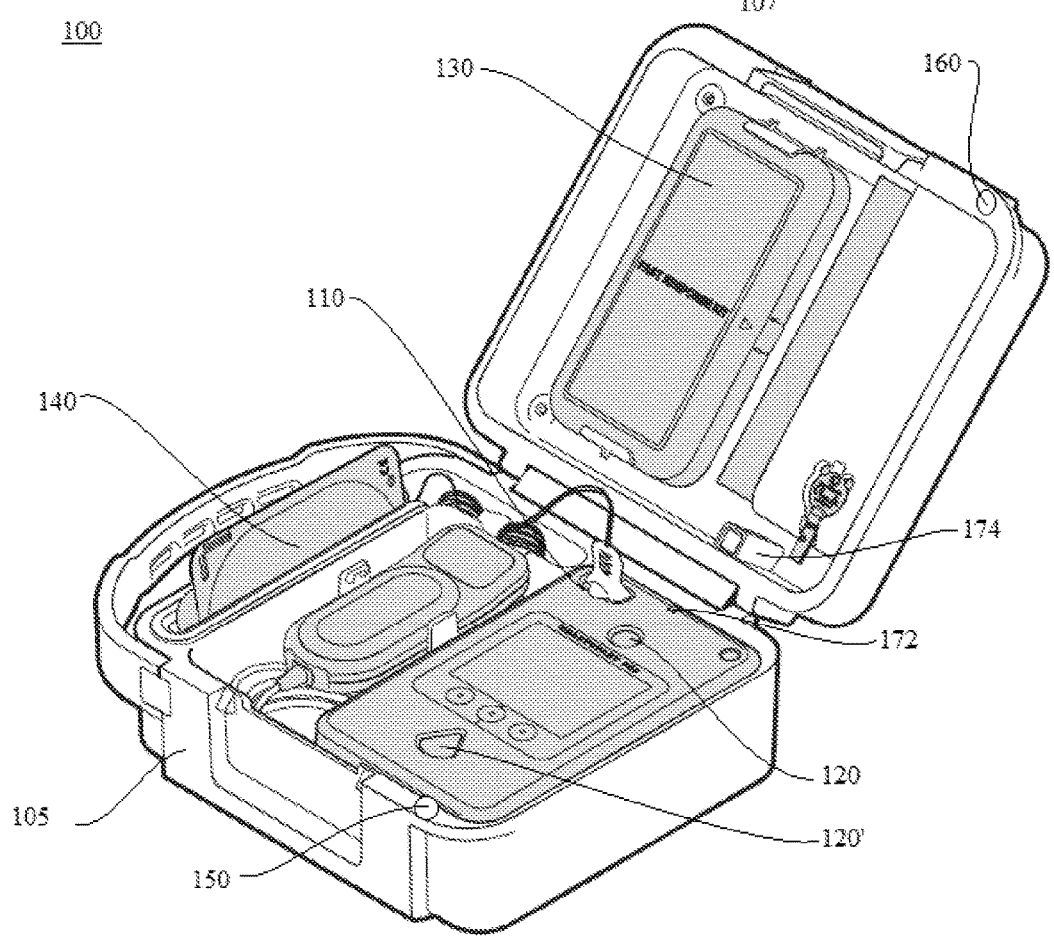
FIG. 1 illustrates a defibrillator apparatus including a carrying case and a case opening sensor, the carrying case in the open position.

Referring first to FIG. 1, a defibrillator apparatus 100 according to the principles of the present invention is shown in the open position. A carrying case 105 having a lid 107 is sized to contain and protect components needed for a cardiac arrest rescue, such as an AED with pre-connected electrodes 140, a CPR meter, and a fast response kit 130. The electrodes are connected to the defibrillator at electrode connector 110 prior to use, in order to reduce the steps needed for deployment and optionally to allow the electrode condition to be periodically tested during storage.

Case 105 preferably comprises a case opening sensor 150. Lid 107 preferably comprises a case open indicator disposed adjacent to sensor 150 when the lid is closed. The case open indicator is preferably a magnet 160, but may also comprise a mechanical button or plunger. Defibrillator 100 thus senses an open lid by the absence of magnet 160 next to sensor 150, and in response automatically turns itself on. It is noted that a corresponding feature that automatically turns portable defibrillator 100 off upon the shutting of lid 107 is preferably avoided, in order to prevent unnecessary delay and confusion involved with an inadvertent lid closure, and unintended defibrillator shutdown, during rescue.

The defibrillator shown in FIG. 1 is preferably disposed to automatically shut itself off and return to a standby state after sensing a long period of time with no activity. No sensed activity may include not sensing a successful deployment of the patient electrodes or not sensing the press of a button. This period of inactivity is called a timeout period, and is preferably on the order of five minutes. Of course, the defibrillator can also be manually shut off by pressing an operator actuated button 120, such as an on/off button 120 or by removing the battery, not shown. The nature of the power down event is recorded in defibrillator memory 218 in a pattern of events file 230, shown in FIG. 2.

FIG. 1 also shows the disposition of a light pipe 174 over ready status indicator light 172. When lid 107 is shut, light pipe 174 overlays ready status light 172. Any indicator light signal on ready status light 172 is then transmitted through light pipe 174 to the exterior of portable defibrillator 100 for ease of viewing without having to open the case.

Figure 2:
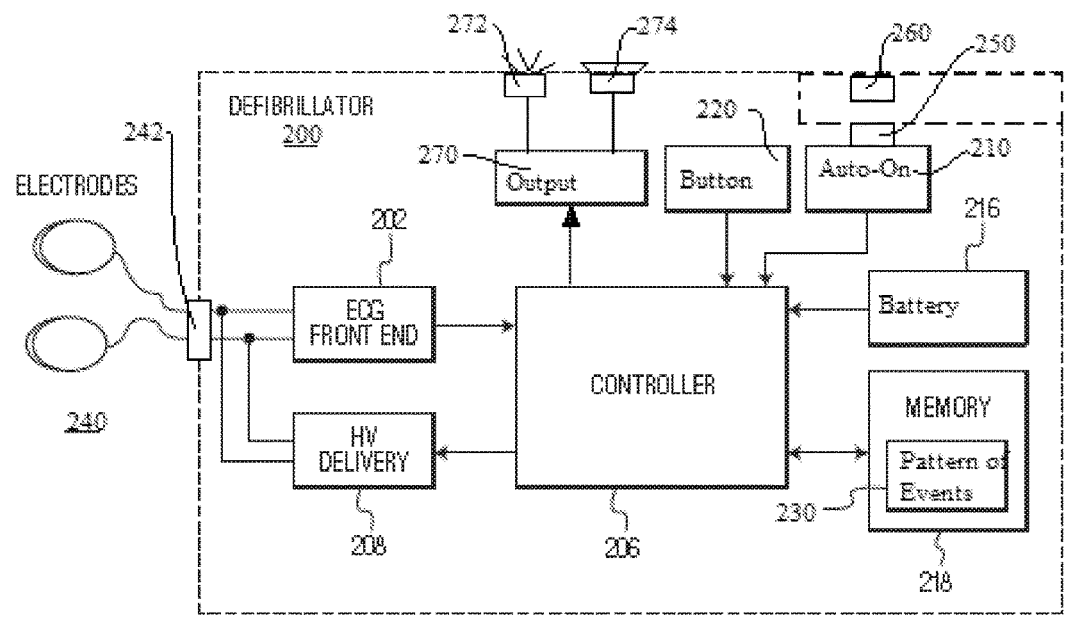
FIG. 2 illustrates a functional circuit diagram according to one embodiment of the invention.

Referring now to FIG. 2, a functional circuit diagram is illustrated to show the function of the inventive defibrillator. Where, equivalent, the FIG. 2 elements correspond in general to the physical components shown in FIG. 1. For example, a pair of electrodes 240 corresponds to the FIG. 1 electrodes 140, etc.

FIG. 2 illustrates a controller 206 which is in electrical communication with each of an electrode connector 242, an operator actuated button 120, and an automatic power on circuit 210. Controller 206 is also in communication with a memory 218 on which is stored a data file 230 containing a pattern of events. Controller 206 is also in communication with a user-perceptible output, which may be an indicator light 270 or a beeper 274. Intervening between controller 206 and electrode connector 242 is an electrode front end 202 which senses a deployment of a set of patient electrodes attached to connector 242, and an electrode high voltage circuit for delivering the defibrillation therapy to the patient via the electrodes.

FIG. 2 also illustrates the automatic power on circuit 210 having a case opening sensor 250, such as a Hall effect sensor, disposed adjacent a magnet 260 or equivalent. Circuit 210 functions to cause controller 206 to activate the defibrillator 200 when the case is opened.

In operation, the automatic power on circuit senses a case opening, and sends an activation signal to controller 206. Controller 206 in turn retrieves data of previous activation events from memory 230. If the previous events combined with the present activation indicate that the activation is the latest in a pattern of events that indicates a repeated inadvertent activation, then controller 206 disables the automatic power on circuit and returns the defibrillator to a standby condition. Return to standby may occur after the timeout period has passed.

In a preferred embodiment, the pattern of events is comprised of a series of detected automatic power on activations followed only by a timeout period deactivation, with no intervening activity. The current activation is preferably included in the series.

Each activation/deactivation may also be required to meet the following criteria:

1. The defibrillator installed battery type is a use battery. This criteria forestalls effects during training, demonstration, or administrative modes of operation;

2. The defibrillator activation must be due to a case latch magnet;

3. The confirmed patient use is detected; and

4. The defibrillator deactivation to standby is with no or poor electrode pads contact or with no intervening On/Off button press or with no Off softkey press during shutdown.

The last criterion allows for continued automatic power on functionality in environments where the defibrillator case is periodically opened to check its contents and/or expiration dates. If a button is not pressed prior to closing the case again, audible and visible prompting normally continues, which alerts the checker to reopen the case and to press the "off" button.

Optionally, controller 206 may compare a threshold periodicity criterion against a calculated periodicity of the series data. For example, if each of the activations occurs at about the same time of day, or multiple times of day, the periodicity indicates that the case openings are intentional shift check events. Controller 206 will not consider such a series as a pattern of events for purposes of disabling the automatic power on feature.

Preferably, a series which constitutes a pattern of events comprises five consecutive above-described activations/deactivations. When controller 206 senses the pattern of events, it records a disable event in the memory 230 and disables the defibrillator power on circuit.

In an alternate embodiment, the pattern of events occurs and is detected by controller 206 over a short period of time. Such a pattern of events may be induced, for example, by a faulty case opening sensor or automatic power on circuit that is spuriously activating. This pattern of events may be sensed as an automatic power on activation of the defibrillator into a use mode, followed by one or more additional automatic power on activations during the same use mode period. The activations would occur without any other detected intervening use activity. In this embodiment, controller 206 disables the automatic power on circuit 210 shortly after the last event in the pattern occurs, such as after a set number of sensed automatic power on activations, without waiting for the end of the timeout period.

When the circuit 210 is disabled, any subsequent opening of the defibrillator case leaves the defibrillator in standby until it is manually activated by a user action. Such user action includes pressing the on/off button 120, pressing a shock button 120', or deploying the patient electrodes 240. When controller 206 senses the user action, the defibrillator is activated for use with no further delay.

Optionally, a user indication at user perceptible output 270 may be issued by controller 206 during the periods when the automatic power on circuit 210 is disabled. The indication may be a flashing light at indicator light 272 or an aural alert when the case is opened at beeper 274.

Controller 206 may subsequently re-enable the automatic power on circuit 210 when the defibrillator is manually activated. Thus, a sensed press of the operator actuated button, or a sensed deployment of the electrodes at electrode connector 242 may reset the pattern of events file in memory, and the series detection will begin again.

Figure 3:
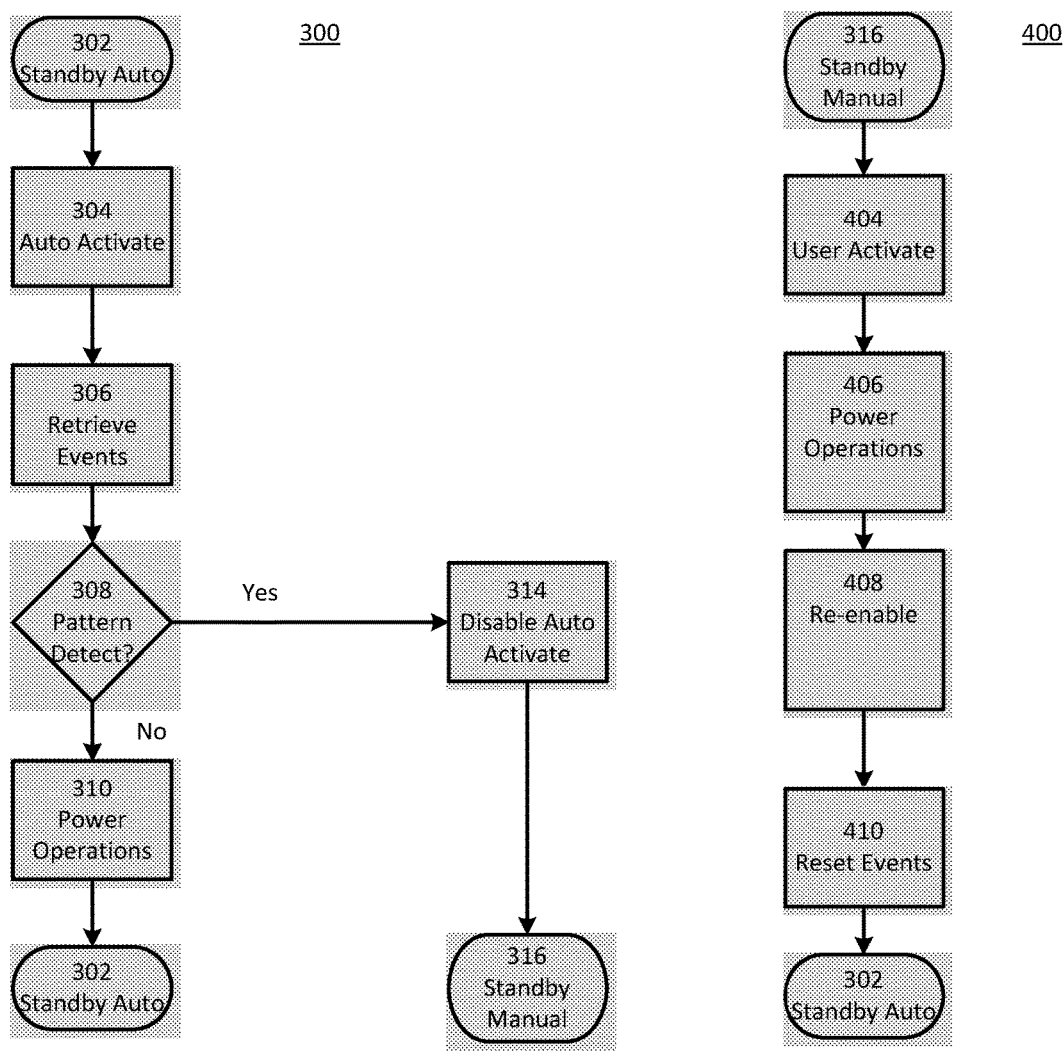
FIG. 3 is a flow chart illustrating one embodiment of the inventive method.

FIG. 3 illustrates a method 300 for managing a power condition of a defibrillator corresponding to the above-described defibrillator functionality. The method 300 begins at step 302 wherein the defibrillator is in a standby mode of operation with an automatic power on feature enabled. At step 304, the automatic power on feature activates the defibrillator, responding to a sensed opening of the case lid or an equivalent sensing. Data regarding previous activations of the defibrillator is retrieved from memory at step 306. The data combined with the circumstances of the current activation are analyzed at step 308 to detect a pattern of events as previously described. If such a pattern of events is detected at step 308, then the automatic power on feature is disabled at step 314. The defibrillator then returns to a standby mode of operation at step 316, either immediately or after a timeout period. The defibrillator at step 316 is in a standby state with the automatic power on circuit disabled. Subsequent activations must occur by a manual user action. Such user action includes one of installing a battery, pressing a button, or deploying electrodes.

The automatic power on feature can be re-enabled by means of the re-enabling method 400 as shown in FIG. 3. The defibrillator is in the standby state at step 316, upon which a user manually activates the defibrillator at step 404 by the manual action. The defibrillator operates in a use state, e.g. for defibrillation, at step 406 as intended by the user. At step 408, the controller re-enables the automatic power on feature, and optionally resets the series of activation events in memory at step 410. When the use is complete, the defibrillator is again placed into the standby state at step 302, having the automatic power on feature activated.

Several variations within the scope of the afore-described invention will readily occur to those skilled in the art. For instance, the defibrillator may include an administrative option to modify the pattern of events which would cause the disabling step to conform to a local practice. The feature could be selectable altogether by an administrator as well. In addition, the precise mode of sensing an automatic activation may vary, such as by means of a latch pull, sensing of a case motion, etc. Other parameters of the pattern of events criteria, such as the threshold number of activations without intervening activity, could also be modified to adjust the sensitivity and specificity of the disabling feature as desired by the user.

The invention claimed is:

1. A portable defibrillator apparatus comprising:
    an electrode connector;
    an operator actuated button;
    an automatic power on circuit operable to actuate the defibrillator independent of the operator actuated button in response to an activation input; and
    a controller in electrical communication with the electrode connector, the operator actuated button and the automatic power on circuit, the controller operable to detect a pattern of activation events and further operable to disable the automatic power on circuit in response to the detected pattern of activation events.

2. The apparatus of claim 1, wherein the pattern of activation events is a plurality of actuations by the automatic power on circuit without an intervening sensed press of the operator actuated button.

3. The apparatus of claim 2, wherein the controller is further operable to re-enable the automatic power on circuit in response to a sensed press of the operator actuated button.

4. The apparatus of claim 2, wherein the plurality of actuations by the automatic power on circuit is less periodic than a threshold periodicity.

5. The apparatus of claim 1, wherein the pattern of activation events is a plurality of actuations by the automatic power on circuit without an intervening sensed deployment of electrodes at the electrode connector.

6. The apparatus of claim 5, wherein the controller is further operable to re-enable the automatic power on circuit in response to a sensed deployment of electrodes at the electrode connector.

7. The apparatus of claim 1, further comprising a user-perceptible output operable to indicate when the automatic power on circuit is disabled.

8. A portable dearillator apparatus comprising:
    an electrode connector;
    an operator actuated button;
    an automatic power on circuit operable to actuate the defibrillator independent of the operator actuated button in response to an activation input; and
    a controller in electrical communication with the electrode connector, the operator actuated button and the automatic power on circuit, the controller operable to detect a pattern of activation events and further operable to disable the automatic power on circuit in response to the detected pattern of activation events,
    wherein the automatic power on circuit further comprises a case opening sensor which actuates when a storage case for the defibrillator is opened.

9. The carrying case of claim 8 wherein the case opening sensor is a Hall effect sensor.

10. A method for managing a power condition of a defibrillator, comprising the steps of:
    providing a defibrillator in a low power standby condition, the defibrillator including a controller in electrical communication with an electrode connector, an operator actuated button, and an automatic power on circuit operable to actuate the defibrillator independent of the operator actuated button in response to an activation input;
    automatically activating the defibrillator with the automatic power on circuit;
    detecting a pattern of events based on the automatically activating step;

disabling the automatic power on circuit based on the detecting step; and returning the defibrillator to the low power standby condition with the automatic power on circuit disabled.

11. The method of claim 10, wherein the pattern of events comprises the automatically activating step and at least one previous automatically activating step without an intervening detection of a user handling event.

12. The method of claim 11, wherein the user handling event comprises one of a deployment of an electrode connected to the electrode connector or a sensed actuation of the operator actuated button.

13. The method of claim 11, wherein the pattern of events further comprises a timeout deactivation step immediately following the previous automatically activating step.

14. The method of claim 10, wherein the pattern of events comprises four previous automatically activating steps each followed by a timeout deactivation step and a fifth timeout deactivation step following the automatically activating step without a detection of an intervening user handling event.

15. The method of claim 10, wherein the pattern of events comprises a plurality of automatically activating steps with neither of an intervening user handling event nor an intervening timeout deactivation step.

16. The method of claim 10, further comprising the steps of:

sensing a user handling event subsequent to the disabling step; and re-enabling the automatic power on circuit based on the sensing step.

17. The method of claim 16, wherein the sensed user handling event is one of a sensed actuation of the operator actuated button or a sensed battery insertion.

18. The method of claim 17, wherein the operator actuated button is one of an on/off button or a shock button.

* * * * *